US009558732B2

(12) United States Patent
Waite et al.

(10) Patent No.: US 9,558,732 B2
(45) Date of Patent: Jan. 31, 2017

(54) ACTIVE NOISE CONTROL SYSTEM

(75) Inventors: Thomas C. Waite, Des Moines, IA (US); Atul G. Kelkar, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 2668 days.

(21) Appl. No.: 12/189,967

(22) Filed: Aug. 12, 2008

(65) Prior Publication Data

US 2009/0010447 A1 Jan. 8, 2009

Related U.S. Application Data

(60) Provisional application No. 60/956,059, filed on Aug. 15, 2007.

(51) Int. Cl.

*A61F 11/06* (2006.01)
*G10K 11/16* (2006.01)
*G10K 11/178* (2006.01)

(52) U.S. Cl.

CPC ... *G10K 11/1788* (2013.01); *G10K 2210/1081* (2013.01)

(58) Field of Classification Search

CPC .............. H04R 1/1083; H04R 2460/01; H04R 2460/13; H04R 25/70; H04R 2410/05; H04R 2410/01; G10K 2210/3028; G10L 21/0208; G10L 2021/02165

See application file for complete search history.

(56) References Cited

U.S. PATENT DOCUMENTS 4,455,675 A 6/1984 Bose et al.
4,494,074 A 1/1985 Bose
4,644,581 A 2/1987 Sapiejewski
4,654,871 A * 3/1987 Chaplin et al. ................. 381/72
4,985,925 A 1/1991 Langberg et al.
5,181,252 A 1/1993 Sapiejewski et al.
5,305,387 A 4/1994 Sapiejewski
5,333,206 A 7/1994 Koss
5,754,662 A * 5/1998 Jolly et al. ................... 381/71.4
5,809,156 A 9/1998 Bartels et al.
5,815,582 A 9/1998 Claybaugh et al.
5,949,897 A 9/1999 Bartels et al.

(Continued)

OTHER PUBLICATIONS

Hendra Tjahyadi et al., Vibration Control of a Cantilever Beam Using Adaptive Resonant Control, paper, 2004, 5 pages, pp. 1776-1780, 5th Asian Control Conference.

(Continued)

*Primary Examiner* — Marlon Fletcher

(74) *Attorney, Agent, or Firm* — Reinhart Boerner Van Deuren P.C.

(57) ABSTRACT

An active noise control system includes a first microphone, a controller operably coupled to the first microphone, and a speaker operably coupled to the controller. The first microphone senses a sound input in an audible spectrum, wherein the sound input includes a disturbance noise portion. The controller includes a selection unit and an output unit. The selection unit determines the disturbance noise portion of the sound input based on a highest frequency level of the sound input. The output unit removes the disturbance noise portion from the sound input to generate a filtered sound input. The speaker generates a speaker output based on the filtered sound input.

20 Claims, 6 Drawing Sheets

(56) References Cited

U.S. PATENT DOCUMENTS

| | | | | |
|---|---|---|---|---|
| 6,122,383 | A | 9/2000 | Berge | |
| 6,396,930 | B1 * | 5/2002 | Vaudrey et al. | 381/60 |
| 6,454,226 | B2 | 9/2002 | Epping et al. | |
| 6,498,858 | B2 * | 12/2002 | Kates | 381/318 |
| 6,597,792 | B1 | 7/2003 | Sapiejewski et al. | |
| 6,829,363 | B2 * | 12/2004 | Sacha | 381/315 |
| 6,831,984 | B2 | 12/2004 | Sapiejewski | |
| 7,139,401 | B2 * | 11/2006 | Culman et al. | 381/71.7 |
| 7,366,315 | B2 * | 4/2008 | Blamey et al. | 381/312 |
| 2003/0059073 | A1 * | 3/2003 | Bren et al. | 381/312 |
| 2003/0123675 | A1 * | 7/2003 | Culman et al. | 381/71.1 |
| 2003/0152243 | A1 * | 8/2003 | Julstrom et al. | 381/315 |
| 2003/0215105 | A1 * | 11/2003 | Sacha | 381/312 |
| 2003/0228019 | A1 * | 12/2003 | Eichler et al. | 381/71.8 |
| 2004/0202336 | A1 * | 10/2004 | Watson et al. | 381/92 |
| 2006/0222192 | A1 * | 10/2006 | Matthey | 381/312 |
| 2008/0137874 | A1 * | 6/2008 | Christoph | 381/57 |
| 2008/0317254 | A1 * | 12/2008 | Kano | 381/71.4 |
| 2009/0010447 | A1 * | 1/2009 | Waite et al. | 381/71.6 |
| 2009/0046868 | A1 * | 2/2009 | Engle et al. | 381/74 |
| 2009/0136052 | A1 * | 5/2009 | Hohlfeld et al. | 381/71.1 |
| 2010/0278352 | A1 * | 11/2010 | Petit et al. | 381/71.1 |
| 2012/0177205 | A1 * | 7/2012 | Bramslow et al. | 381/23.1 |

OTHER PUBLICATIONS

Sen M. Kuo et al., Active Noise Control System for Headphone Applications, paper, Mar. 2006, 5 pages, pp. 331-335, IEEE Transactions on Control Systems Technology, vol. 14, No. 2.

B. Rafaely et al., Broadband performance of an active headrest, paper, 7 pages, pp. 787-793, J. Acoust. Soc. Am. 106 (2), Aug. 1999.

Boaz Rafaely et al., $H_2/H\infty$ Active Control of Sound in a Headrest: Design and Implementation, paper, Jan. 1999, 6 pages, pp. 79-84, IEEE Transactions on Control Systems Technology, vol. 7, No. 1.

* cited by examiner

ACTIVE NOISE CONTROL SYSTEM

CROSS-REFERENCE TO RELATED PATENT APPLICATIONS

This patent application claims the benefit of U.S. Provisional Patent Application Ser. No. 60/956,059, filed Aug. 15, 2007, the entire teachings and disclosure of which are incorporated herein by reference thereto.

STATEMENT REGARDING FEDERALLY SPONSORED RESEARCH AND DEVELOPMENT

This invention was made in part with Government support under Grant Number CMS 0301740 awarded by the National Science Foundation. The Government has certain rights in this invention.

BACKGROUND

In noise-mitigating headset designs, passive noise control approaches have shown substantial broadband reductions of high frequency noise using well-sealed ear defenders lined with sound absorbing material such as high-density foam. The materials of the headphones themselves also block out some sound waves, especially those at higher frequencies. The sound absorbing material makes them heavier than normal headphones. The tradeoff of all that extra weight is a reduction in noise of about 15 to 20 decibels (dB). In some cases, people working in a noisy environment all day do not wear ear defenders as often times they can be uncomfortable to wear for long periods of time and the headsets tend to limit speech intelligibility.

SUMMARY

In one embodiment, an active noise control system includes a first microphone, a controller operably coupled to the first microphone, and a speaker operably coupled to the controller. The first microphone senses a sound input in an audible spectrum, wherein the sound input includes a disturbance noise portion. The controller includes a selection unit and an output unit. The selection unit determines the disturbance noise portion of the sound input based on a frequency level of the sound input. The output unit removes the disturbance noise portion from the sound input to generate a filtered sound input. The speaker generates a speaker output based on the filtered sound input.

In another embodiment, an earpiece includes a first microphone, a second microphone, a controller, and a speaker. The first microphone senses a sound input in an audible spectrum, wherein the sound input includes a disturbance noise portion. The second microphone is operably coupled to the controller. The second microphone senses an unfiltered sound input. The controller is operably coupled to the first microphone and the second microphone, and includes a selection unit and an output unit. The selection unit determines the disturbance noise portion of the sound input based on a frequency level of the sound input and the unfiltered sound input. The output unit removes the disturbance noise portion to generate a filtered sound input. The speaker is operably coupled to the first microphone. The speaker generates a speaker output based on the filtered sound input.

In yet another embodiment, a method of reducing noise in a predetermined frequency band includes the following steps: sensing a sound input in an audible spectrum, wherein the sound input includes a disturbance noise portion; determining the disturbance noise portion of the sound input based on a frequency level of the sound input; removing the disturbance noise portion from the speaker output to generate a filtered sound input; and generating a speaker output based on the filtered sound input.

Other aspects, objectives and advantages will become more apparent from the following detailed description when taken in conjunction with the accompanying drawings.

BRIEF DESCRIPTION OF THE DRAWINGS

The accompanying drawings incorporated in and forming a part of the specification illustrate several aspects of the present invention and, together with the description, serve to explain the principles of the invention. In the drawings.

While the invention will be described in connection with certain preferred embodiments, there is no intent to limit it to those embodiments. On the contrary, the intent is to cover all alternatives, modifications and equivalents as included within the spirit and scope of the invention as defined by the appended claims.

DETAILED DESCRIPTION

The apparatus described herein is an active noise control system that mitigates acoustic noise in certain frequency bands. The controller requires no design iterations and the gain margin of the resulting loop can be specified ahead of time (the phase margin is always infinite). This controller acts directly on a disturbance rather than damping resonant poles of the system plant. This allows for a notch to be created in the disturbance anywhere in the spectrum and not just at resonant modes of the system.

The system identifies in real-time the loudest frequency in a disturbance signal and adaptively updates a narrow-band resonant filter that is placed in a feedback loop. The net effect is that a notch is created in the audible spectrum, causing significant reductions in the "loudest" frequencies of a disturbing noise. The controller can be configured to control certain frequency ranges in which the disturbance is known while passing desired noises through without being altered.

In one embodiment, the system consists of a headset having a speaker, microphone, and controller implemented in a feedback configuration in close proximity to a user's ear in order to reduce the highest frequency noise of the audible spectrum. The system can be used in dental offices for patients, dental assistants, doctors, in noisy environments such as manufacturing shops, in appliances, in planes, etc.

Figure 1:
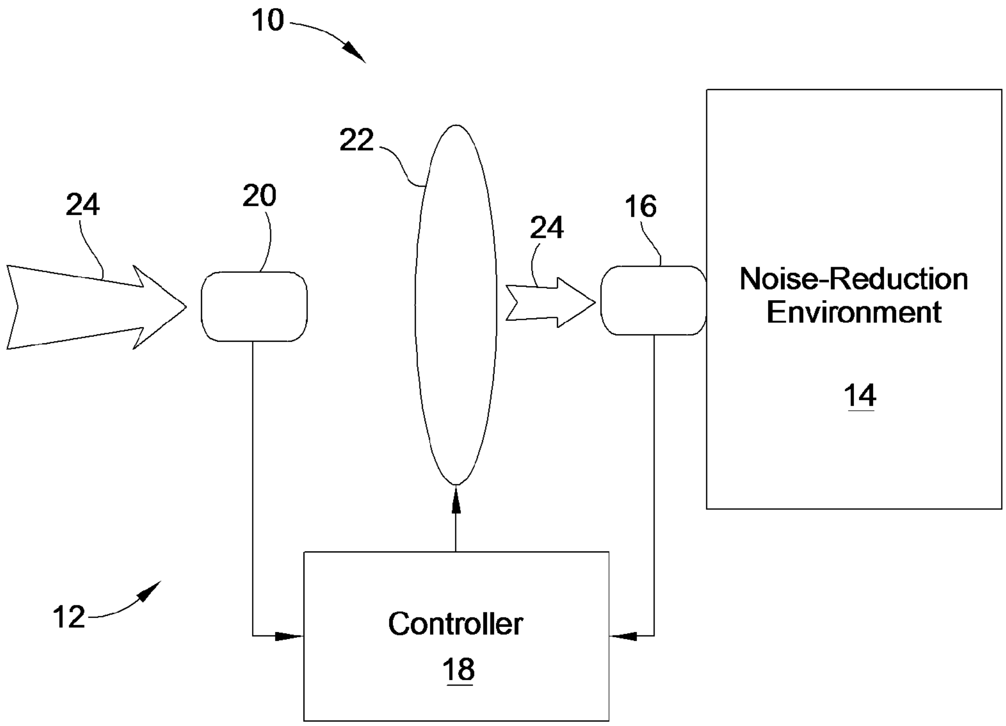
FIG. 1 is an illustration of an exemplary environment in which the active noise control system operates.

Turning to the drawings, wherein like reference numerals refer to like elements, the apparatus is illustrated as being implemented in a suitable environment. FIG. 1 illustrates an environment 10 in which an active noise control system 12 is used to reduce noise in noise reduction environment 14. The active noise control system 12 includes a feedback microphone 16 used by controller 18 in conjunction with reference microphone 20 to control speaker 22. The controller determines the frequencies of the "loudest" incoming noise and reduces the magnitude of the noise as represented by arrows 24. The controller identifies the frequency which corresponds to the loudest part of the disturbance noise. Doing this requires the use of an extra microphone to measure the disturbance noise unchanged by any control action. The microphone used for feedback could not be used because the controller would reduce the noise at one frequency only until the noise level somewhere else in the spectrum was louder by comparison. The adaptation algorithm would then switch the control action to the other frequency only to have the previous frequency's loudness increase again. This would cause the controller to quickly alternate between the two loudest parts of the noise spectrum, achieving very little reduction at either frequency. It is for this reason the feed forward microphone 20 is needed to acquire the disturbance signal for processing.

Figure 2:
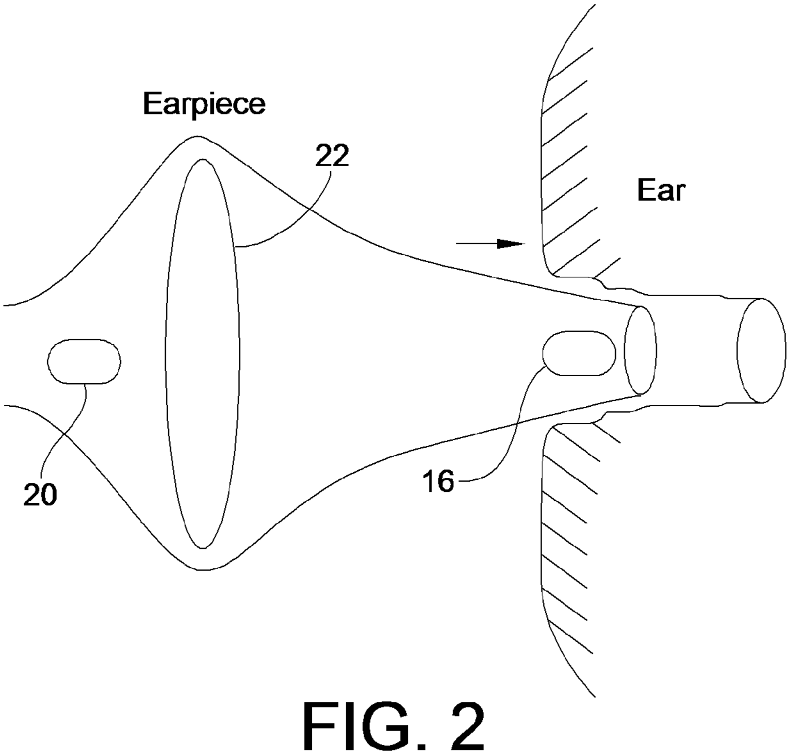
FIG. 2 is an illustration of the active noise control system of FIG. 1 implemented in an earpiece.

The active noise control system shall now be described in an earpiece or headset. FIG. 2 illustrates how an earpiece, which can be part of a headset, is set up using the active noise control system. The feedback microphone 16 must be positioned close to the ear in order for the system to function properly. Additionally, the reference microphone 20 must be sufficiently acoustically isolated from the speaker 22.

The controller 18 is a form of a resonant mode controller that allows a user to decide the robustness of the control by setting the gain margin for the loop transfer function ahead of time. The only design parameter is σ, which essentially determines the shape of the resonant mode controller and consequently the shape of the resulting notch in the noise spectrum. Note that by changing the focus of control to the disturbance frequency rather than the plant resonant mode, more direct control of the disturbance noise is achievable. This is because while a typical resonant controller is capable of damping a resonant mode of the plant, this does not ensure maximum reduction of the disturbance. In fact, if a disturbance is primarily tonal and the dominant tonal frequency does not align with the plant resonant mode, very little noise reduction will occur.

Figure 3:
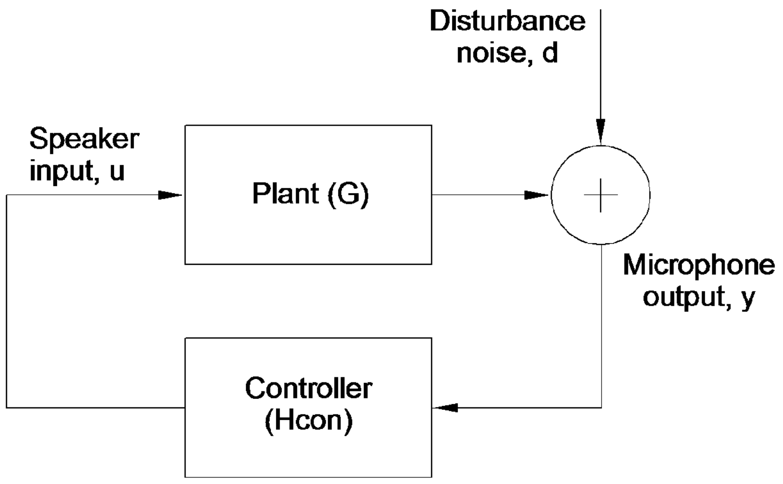
FIG. 3 is a block diagram of a plant and controller in closed-loop configuration.

The plant and controller configuration is shown in FIG. 3. It can be seen that the disturbance transfer function to be that of Equation 1. It is clear from looking at this equation that the loop transfer function, GHcon, needs to be a large and negative value at the resonant frequency in order to minimize the effect of the disturbance at that frequency. Therefore, for optimum disturbance rejection at the resonant frequency, $w_r$, the magnitude should be large and the phase should be at ±π radians.

$$\frac{y}{d} = \frac{1}{1 - GH_{con}} \quad \text{Eq. (1)}$$

By assuming the plant, G, to be of constant gain and phase around a small neighborhood of the resonant mode, the structure of the controller, $H_{con}$, and the loop transfer function, GHcon, can each take the form of a second order resonant mode. This is a reasonable assumption if the resonant mode is chosen to be much undamped (small σ) so the controller gain is very small everywhere except for the resonant peak. Also, the headset system magnitude response is very flat due to the free field nature of the setup and the phase delay is fairly small because of the close proximity between the speaker and feedback microphone. Since each second order resonant mode transfer function is identical in structure, the only difference between controllers is their magnitude and phase at the peak ($w_r$). Therefore, to completely describe the controller, Hcon, one only needs to know its magnitude and phase at the resonant peak. To determine the magnitude and phase of the controller which will lead to the desired loop response, it becomes necessary to solve Equation 2 in terms of both it's magnitude and it's phase evaluated at $w_r$ (Equations 3 and 4).

$$H_{con} = \frac{GH_{con}}{G} \quad \text{Eq. (2)}$$

$$g = |H_{con}(w_r)| = \frac{|GH_{con}(w_r)|}{|G(w_r)|} = \frac{\frac{1}{GM}}{|G(w_r)|} \quad \text{Eq. (3)}$$

$$\phi = \angle H_{con}(w_r) = \angle GH_{con}(w_r) - \angle G(w_r) = \pi - \angle G(w_r) \quad \text{Eq. (4)}$$

Equation 3 shows the magnitude of the loop at $w_r$ is just the reciprocal of the gain margin, GM, and therefore, the controller gain can be directly determined by a user specified gain margin. The desired phase of the loop is shown in Equation 4 to be π radians to ensure negative feedback and maximum disturbance rejection. Note that a plant model is not required in this control since the only values needed are the experimentally obtained frequency response magnitude and phase. Using these two equations enables the direct computation of the magnitude and phase of the controller given only the frequency response data of the plant.

Once the magnitude and phase of the controller at the resonant frequency are calculated, the next step is finding a second order transfer function which will exhibit this same magnitude and phase at its resonant frequency. Equation 5 shows the general second order transfer function of the controller in the discrete domain with sampling time, T. Note that a transfer function with two zeros could also be used but one zero is simpler and just as versatile. The desired magnitude and phase of the controller at resonance will each respectively determine the unknown value of gain, k, and the unknown zero location, a.

$$H_{con} = \frac{k(z-a)}{z^2 - 2ze^{-\sigma T}\cos(w_r T) + e^{2\sigma T}} \quad \text{Eq. (5)}$$

When solving for the magnitude and phase of the transfer function in Equation 5, it becomes necessary to split it into its real and imaginary parts. Once this is done, the gain, k, drops out of the phase calculation and allows the direct calculation of the zero location, a, in terms of the desired phase, ϕ:

$$a = \frac{e^{-\sigma T}\sin(\phi - w_r T) - \sin(\phi + w_r T)}{e^{-\sigma T}\sin(\phi) - \sin(\phi + 2w_r T)} \quad \text{Eq. (6)}$$

where $$\phi = \tan^{-1}\left(\frac{\sin(w_r T)}{\cos(w_r T) - a}\right) - \tan^{-1}\left(\frac{1 - e^{-\sigma T}\sin(2w_r T)}{(1 - e^{-\sigma T})\cos(2w_r T) - e^{-\sigma T} + e^{-2\sigma T}}\right) \quad \text{Eq. (7)}$$

A general gain, g, can be calculated as shown in Equation 8 and 9. This is then solved for the controller gain, k, in terms of the zero location, a, and the magnitude at resonance, g, in Equation 10.

$$g = |H_{con}(w_r)| \quad \text{Eq. (8)}$$

$$g = \frac{k\sqrt{(\cos(w_r T) - a)^2 + \sin^2(w_r T)}}{\sqrt{((1 - e^{-\sigma T})\cos(2w_r T) + e^{-2\sigma T} - e^{-\sigma T})^2 + ((1 - e^{-\sigma T})\sin(2w_r T))^2}} \quad \text{Eq. (9)}$$

$$k = \frac{g\sqrt{((1 - e^{-\sigma T})\cos(2w_r T) + e^{-2\sigma T} - e^{-\sigma T})^2 + ((1 - e^{-\sigma T})\sin(2w_r T))^2}}{\sqrt{a^2 - 2a\cos(w_r T) + 1}} \quad \text{Eq. (10)}$$

Now that the unknowns, a and k, are explicitly solved for in Equations 6 and 10, respectively, the controller has a closed form solution. Finally, substituting for g and ϕ, Hcon can be written in terms of the magnitude and phase of the plant at the resonant frequency as indicated in Equations 11-13. This means the entire transfer function of Hcon can be calculated using only the plant frequency response data as input. The designer is able to specify the sampling time, T, the controller shape (given by σ), and most importantly the gain margin of the resulting loop transfer function, GM.

$$H_{con} = \frac{k(z - a)}{z^2 - 2ze^{-\sigma T}\cos(w_r T) + e^{-2\sigma T}} \quad \text{Eq. (11)}$$

$$a = \frac{e^{-\sigma T}\sin(w_r T + \angle G(w_r)) + \sin(w_r T - \angle G(w_r))}{e^{-\sigma T}\sin(\angle G(w_r)) + \sin(2w_r T - \angle G(w_r))} \quad \text{Eq. (12)}$$

$$k = \frac{\sqrt{((1 - e^{-\sigma T})\cos(2w_r T) + e^{-2\sigma T} - e^{-\sigma T})^2 + ((1 - e^{-\sigma T})\sin(2w_r T))^2}}{GM|G(w_r)|\sqrt{a^2 - 2a\cos(w_r T) + 1}} \quad \text{Eq. (13)}$$

The preceding paragraphs have demonstrated a method for finding a single controller, $H_{con}$, at a desired frequency, $w_r$, using plant frequency response data obtained at that frequency. Since spectrum analyzers have the ability to obtain plant frequency response information at many data points across a large frequency range. It is therefore a logical extension to evaluate multiple controllers at multiple data points across the entire frequency range, calculating one controller at each point where plant magnitude and phase data can be experimentally obtained. For example, a typical spectrum analyzer used to take plant frequency response data is able to take up to 800 points of data, which means 800 different controllers can be calculated in a single sweep. The frequency response of the headset can be obtained in the audible frequency range (e.g., from 500-13300 Hz,) so a controller can be calculated every 16 Hz.

Figure 4:
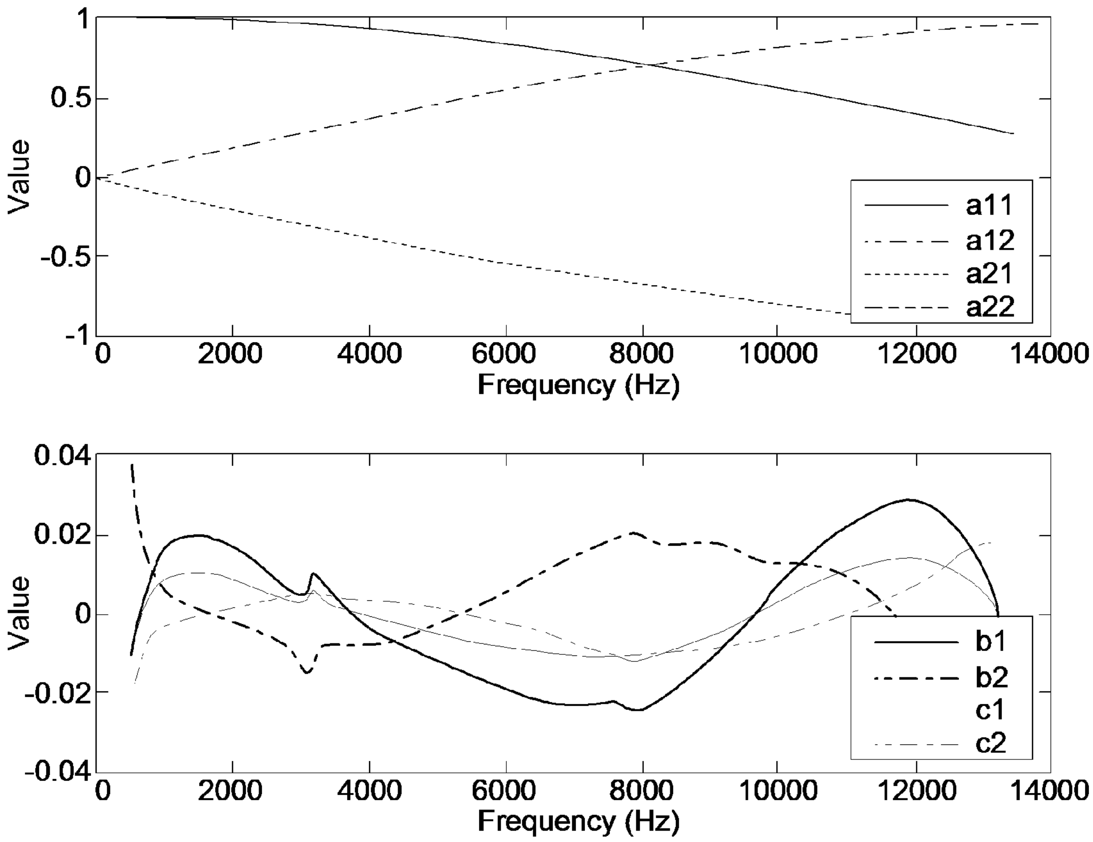
FIG. 4 is a graph illustrating controller matrix elements as a function of frequency.

With a representative sampling of controllers across the entire region of interest, an adaptive technique can be implemented which intelligently switches between controllers based on the disturbance noise. A method of updating state-space coefficients shall be used to implement an adaptive switching technique. Note that other schemes can be used. For example, the switching scheme can just as easily been accomplished by updating transfer function coefficients. In the state-space updating technique, the modal canonical state-space descriptions of each controller are calculated and can be shown as frequency dependent curves (see FIG. 4). Some manipulation of these matrix elements may be necessary to obtain a smooth curve since modal state-space form can yield four different representations from a single controller as shown in Equation 14. Having a smooth curve is important if linear interpolation between identified frequencies is used in the adaptive algorithm, so using a consistent modal matrix form is generally required.

$$H_{con} = \left[\begin{array}{cc|c} a_{11} & a_{12} & b_1 \\ a_{21} & a_{22} & b_2 \\ \hline c_1 & c_2 & 0 \end{array}\right] = \left[\begin{array}{cc|c} a_{11} & a_{12} & -b_1 \\ a_{21} & a_{22} & -b_2 \\ \hline -c_1 & -c_2 & 0 \end{array}\right] = \left[\begin{array}{cc|c} a_{11} & a_{12} & -b_2 \\ a_{21} & a_{22} & b_1 \\ \hline -c_2 & c_1 & 0 \end{array}\right] = \left[\begin{array}{cc|c} a_{11} & a_{12} & b_2 \\ a_{21} & a_{22} & -b_1 \\ \hline c_2 & -c_1 & 0 \end{array}\right] \quad \text{Eq. (14)}$$

Figure 5:
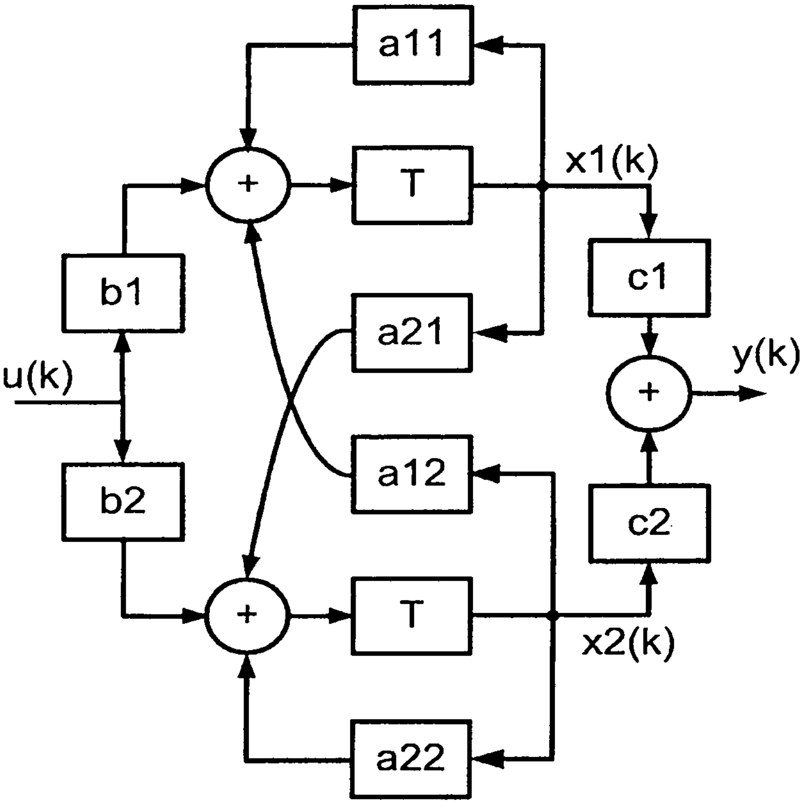
FIG. 5 is a simulation block diagram of $H_{con}$ with adaptive state-space variables.

Implementation of the simulation diagram of FIG. 5 allows for real-time updates of the controller state-space matrix elements. This simulation diagram is an input-output description of the adaptive state-space representation of $H_{con}$ where T denotes a single sample delay. FIG. 5 shows how each discrete input sample from the microphone is manipulated by these values before being output to the speaker 22. Each element ($a_{11}$; $a_{12}$; $a_{21}$; $a_{22}$; $b_1$; $b_2$; $c_1$; $c_2$) can be updated as the loudest frequency of the disturbance changes.

Figure 6:
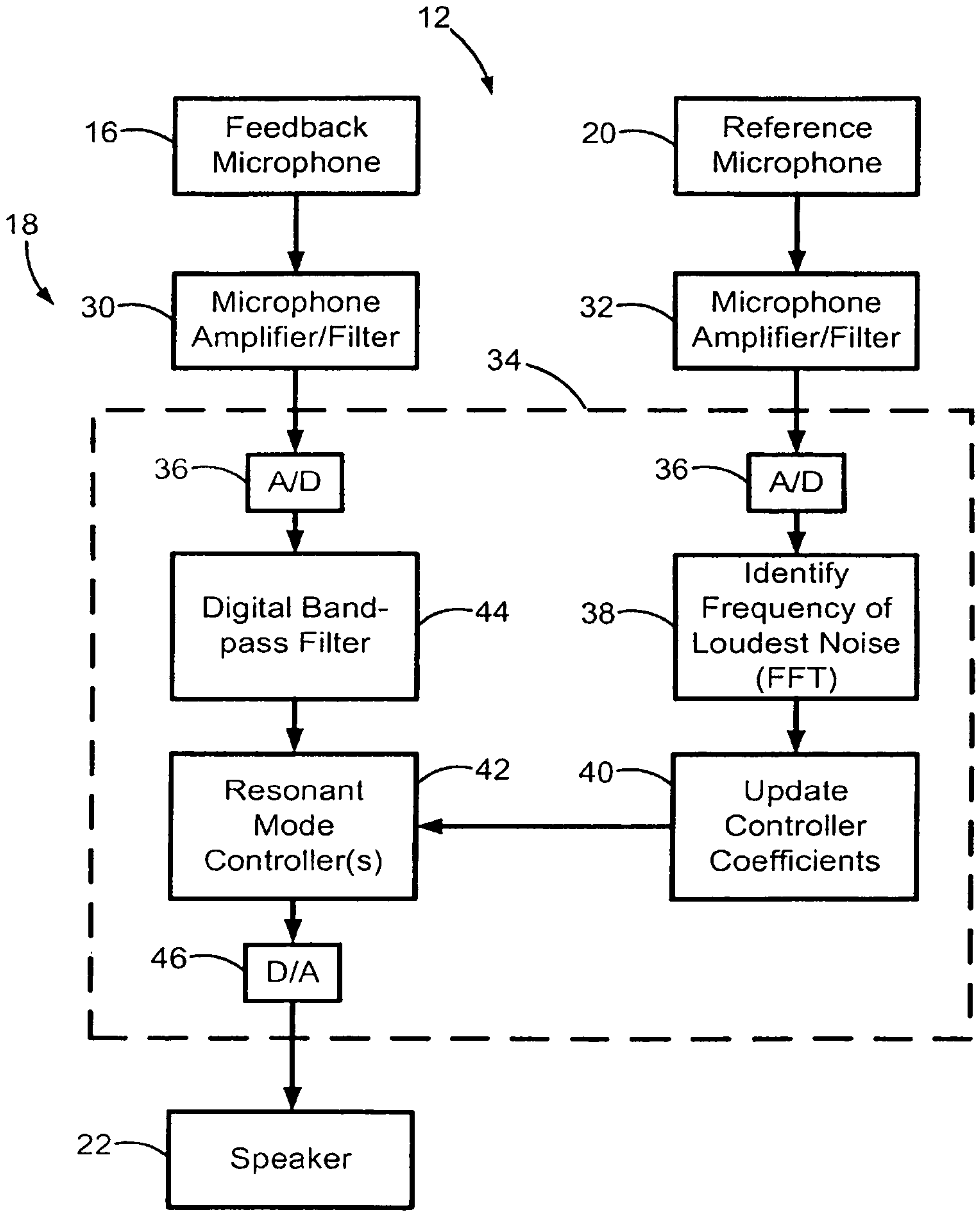
FIG. 6 is a block diagram of an implementation of an active noise control system in accordance with the teachings of the present invention.
Figure 7:
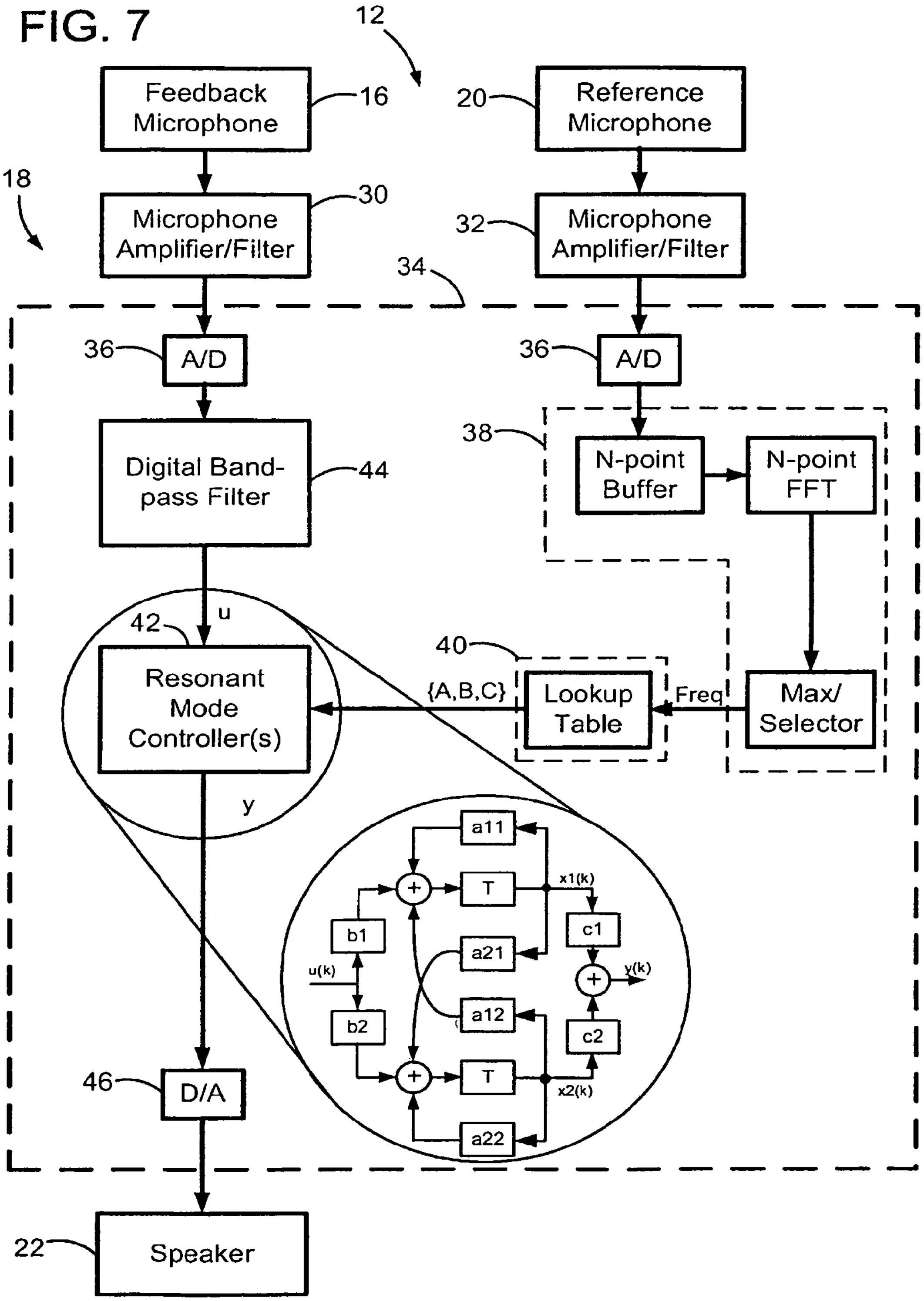
FIG. 7 is a block diagram of an implementation of an active noise reduction controller.

Now that the details of the active noise control system have been described, the controller 18 shall now be described. Turning now to FIGS. 6 and 7, a block diagram of one implementation of controller 18 is shown. The controller 18 amplifies and filters the feedback microphone 16 and reference microphone 20 in blocks 30, 32 respectively. Blocks 30, 32 amplify the respective microphone signal to an acceptable voltage level and filter the resulting signal to minimize electronic interference (e.g., 60 Hz) and unnecessary high frequency noise. The amplified and filtered signals are input into digital controller 34 and converted into digital signals by Analog to Digital converters 36.

In block 38, the reference signal is buffered and a Fourier transform is taken so that one or more frequencies corresponding to the loudest portion(s) of the disturbance signal are identified and selected for reduction. Other methods for detecting the most dominating frequencies of noise could also be used. Note that the frequencies selected should be sufficiently spaced (e.g., approximately 1 KHz spacing at high frequencies) for the controller to be more effective.

In block 40, the frequencies chosen are used to select and update controller coefficients (e.g., $a_{11}$; $a_{12}$; $a_{21}$; $a_{22}$; $b_1$; $b_2$; $c_1$; $c_2$). In one embodiment, a look up table is used to select the coefficients. Alternative methods may be used. The coefficients are simultaneously updated in the resonant mode controller 42, which makes the resonant mode controller 42 adaptive to a changing disturbance noise. A digital implementation of a second order resonant mode controller is shown in the blown-up portion of FIG. 7 and in FIG. 5, where T indicates a sample delay. When multiple notches in the disturbance spectrum are desired, multiple resonant mode controllers operate in parallel and each of their outputs are added together before being sent to the speaker 22.

The input to the resonant mode controller(s) is the feedback signal after it has passed through a low order band-pass filter 44. This filter is used to focus the control effort on the disturbance noise band and limit its effect on a desired noise band. The resulting output signal of the resonant mode controller is converted to an analog signal via digital to analog converter 46 and output to the speaker 22 to create a notch in the noise spectrum at the desired frequencies.

Now that the functionality of the system has been described, experimental results shall be described. In one experiment, a Simulink block diagram of the adaptive controller was uploaded onto a real-time I/O board from dSpace. Two 12 bit A/D microphone inputs and one 14 bit D/A speaker output were used. The feedforward microphone input of the disturbance noise was buffered and a 4096 point FFT (Fast Fourier Transform) was performed every 1/16th of a second to determine the frequency of the noise which was the loudest. This provided a ±8 Hz resolution for determining $w_r$. There is a tradeoff between the number of times in which the controller can be updated and the resolution of the identified frequency. This tradeoff is shown in Table 1. If the tonal noise is fairly constant over time, identification of the tonal frequency can be made with a high level of accuracy. However, if the disturbance noise is known to have a quickly varying tonal frequency, lower resolution is to be expected.

TABLE 1

| Number of Points | Update Rate (sec) | Resolution (Hz) |
|---|---|---|
| 1024 | 1/64 | ±32 |
| 2048 | 1/32 | ±16 |
| 4096 | 1/16 | ±8 |
| 8192 | 1/8 | ±4 |
| 16384 | 1/4 | ±2 |
| 32768 | 1/2 | ±1 |
| 65536 | 1 | ±0.5 |

The plant magnitude and phase data was obtained from 500-13300 Hz at 16 Hz increments using the spectrum analyzer. This data was used as input to find the appropriate controllers as described above. A sampling rate of 65536 Hz, a controller shape of $\sigma$=40, and a loop gain margin of 6 dB were chosen as parameters. The test set-up used a mannequin head equipped with a microphone in the ear to acoustically mimic what a person would hear. An earpiece design such as the one illustrated in FIG. 2 was used. A high frequency tonal noise source (e.g., a dental drill) was turned on in front of the mannequin head just outside the mannequin ear.

Figure 8:
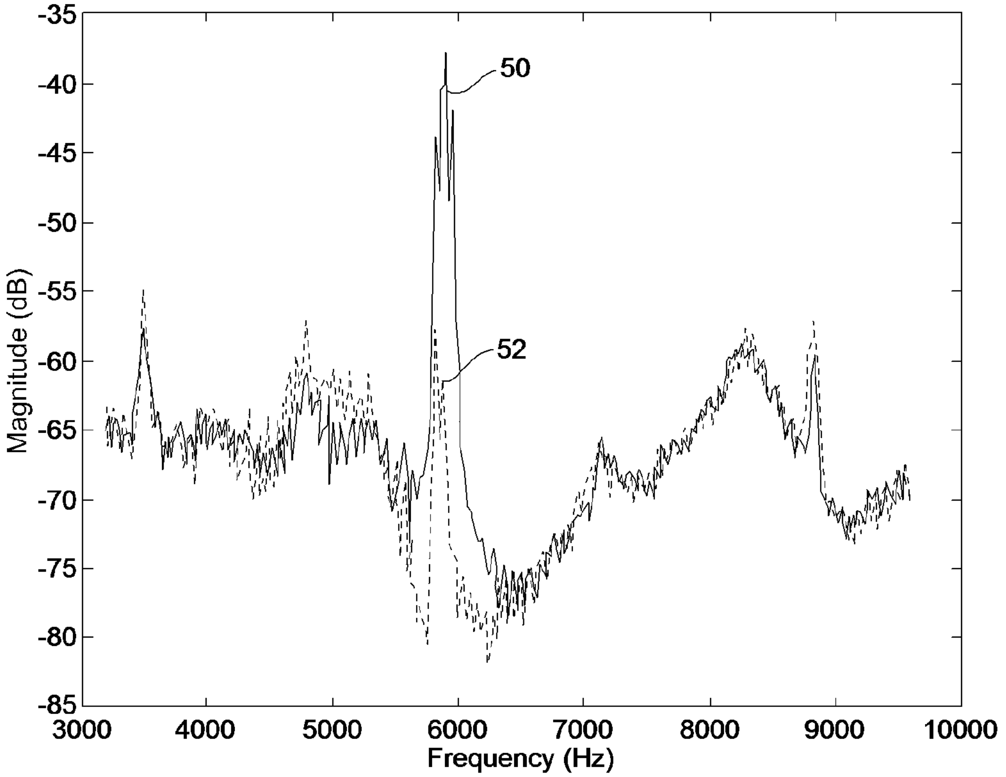
FIG. 8 is a graph illustrating how the active noise control system described herein reduces peak noise in a noise spectrum.

FIG. 8 shows the averaged spectrum of the disturbance before and after control as the frequency of the primary tone of the disturbance varied rapidly from 5800-6000 Hz. Waveform 50 shows an averaged spectrum with the active noise control system presented herein turned off and waveform 52 shows an averaged spectrum with the system turned on. It can be seen that the primary tone was reduced. The performance of the adaptive controller shows approximately 20 dB of reduction at the primary tone with at most 5 dB increase in noise elsewhere in the spectrum.

Figure 9:
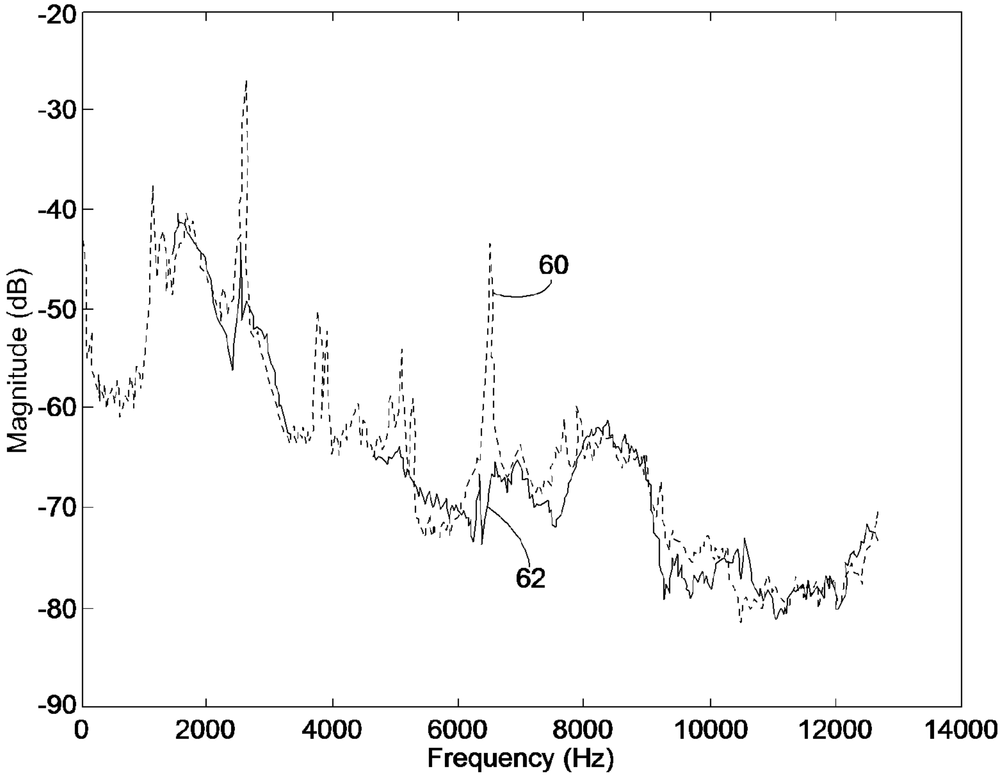
FIG. 9 is another graph illustrating how the active noise control system described herein reduces peak noise in a noise spectrum.

FIG. 9 illustrates a spectrum of drill noise being reduced. Waveform 60 shows an averaged spectrum with the active noise control system presented herein turned off and waveform 62 shows an averaged spectrum with the system turned on. It can be seen that the peaks at approximately 2500 and 6500 Hz have been substantially reduced.

From the foregoing, it can be seen that the apparatus described provides a method for determining resonant mode controllers which allows for direct control of a disturbance. While standard resonant controllers are used for damping fixed resonant poles of the system plant, the present resonant mode controller creates a notch in the disturbance at any frequency. A closed form solution allows a user to specify the gain margin of the resulting loop response. Using the frequency response data of the plant, multiple resonant controllers are identified so the adaptive controller can switch between them based on the loudest disturbance frequency. Test results show large reductions of high frequency tonal disturbances.

The use of the terms “a” and “an” and “the” and similar referents in the context of describing the invention (especially in the context of the following claims) is to be construed to cover both the singular and the plural, unless otherwise indicated herein or clearly contradicted by context. The terms “comprising,” “having,” “including,” and “containing” are to be construed as open-ended terms (i.e., meaning “including, but not limited to,”) unless otherwise noted. All methods described herein can be performed in any suitable order unless otherwise indicated herein or otherwise clearly contradicted by context. The use of any and all examples, or exemplary language (e.g., “such as”) provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An active noise control system, comprising:

a first microphone configured to sense a sound input in an audible spectrum, wherein the sound input comprises a disturbance noise portion;

a controller operably coupled to the first microphone, the controller comprising a selection unit and an output unit operably coupled to the selection unit, wherein the selection unit is configured to determine the disturbance noise portion of the sound input based on a highest frequency level of the sound input, and wherein the output unit is configured to remove the disturbance noise portion from the sound input to generate a filtered sound input; and a speaker operably coupled to the controller, the speaker configured to generate a speaker output based on the filtered sound input.

2. The active noise control system of claim 1, wherein the controller is an adaptive feedback controller to generate the filtered sound input.

3. The active noise control system of claim 1, wherein the controller is a resonant mode controller that implements adaptive feedback control to generate the filtered sound input.

4. The active noise control system of claim 3, wherein the selection unit determines the disturbance noise portion based on a Fourier transform, and wherein the output unit changes one or more coefficients to adapt to a change in the disturbance noise portion.

5. The active noise control system of claim 1, wherein the controller comprises a plurality of controllers operating in parallel to remove a plurality of disturbance noise portions from the sound input.

6. The active noise control system of claim 1, further comprising a second microphone operably coupled to the controller and located upstream to the first microphone, wherein the second microphone is configured to sense an unfiltered sound input, and wherein the controller is configured to determine the disturbance noise portion of the sound input based on both the highest frequency level of the sound input and the unfiltered sound input.

7. The active noise control system of claim 1, wherein the first microphone is located in close proximity to a user's ear.

8. An earpiece, comprising:

a first microphone configured to sense a sound input in an audible spectrum, wherein the sound input comprises a disturbance noise portion;

a second microphone operably coupled to the controller and located upstream to the first microphone, the second microphone configured to sense an unfiltered sound input;

a controller operably coupled to the first microphone and the second microphone, the controller comprising a selection unit and an output unit operably coupled to the selection unit, wherein the selection unit is configured to determine the disturbance noise portion of the sound input based on a highest frequency level of the sound input and the unfiltered sound input, and wherein the output unit is configured to remove the disturbance noise portion to generate a filtered sound input; and a speaker operably coupled to the first microphone and configured to generate a speaker output based on the filtered sound input.

9. The earpiece of claim 8, wherein the controller is a resonant mode controller that implements adaptive feedback control.

10. The earpiece of claim 9, wherein the selection unit determines the disturbance noise portion based on a Fourier transform, and wherein the output unit adapts to a change in the disturbance noise portion by changing one or more coefficients.

11. The earpiece of claim 8, wherein the controller comprises a plurality of controllers operating in parallel to remove a plurality of disturbance noise portions of the sound input.

12. The earpiece of claim 8, further comprising a second microphone operably coupled to the controller and located upstream to the first microphone, the second microphone configured to sense an unfiltered sound input.

13. The earpiece of claim 8, wherein the first microphone is located in close proximity to a user's ear.

14. A method of reducing noise in a predetermined frequency band, the method comprising the steps of:

sensing a sound input in an audible spectrum, wherein the sound input comprises a disturbance noise portion;

determining the disturbance noise portion of the sound input based on a highest frequency level of the sound input;

removing the disturbance noise portion from the speaker output to generate a filtered sound input; and generating a speaker output based on the filtered sound input.

15. The method of claim 14, wherein the step of removing the disturbance noise portion comprises the step of implementing an adaptive feedback control.

16. The method of claim 14, wherein the step of determining the disturbance noise portion comprises the step of determining the disturbance noise portion based on a Fourier transform.

17. The method of claim 14, wherein the step of removing the disturbance noise portion comprises the step of adapting to a change in the disturbance noise portion.

18. The method of claim 17, wherein the step of adapting to the change in the disturbance noise portion comprises the step of updating one or more coefficients.

19. The method of claim 14, further comprising the step of operating a plurality of controllers in parallel to remove a plurality of disturbance noise portions of the sound input.

20. The method of claim 14, further comprising the steps of:

sensing an unfiltered sound input at a second microphone; and determining the disturbance noise portion of the sound input based on the highest frequency level of both the sound input and the unfiltered sound input.

* * * * *